United States Patent [19]

Cebrian

[11] 3,991,211

[45] Nov. 9, 1976

[54] SELECTIVE CELL NECROSIS IN EXPERIMENTAL ANIMAL TUMORS

[75] Inventor: Gregorio Ramon Cebrian, Madrid, Spain

[73] Assignee: Fundacion de Estudios Farmaco-Biologicos, Madrid, Spain

[22] Filed: June 4, 1973

[21] Appl. No.: 366,360

Related U.S. Application Data

[60] Division of Ser. No. 201,331, Nov. 23, 1971, abandoned, which is a continuation-in-part of Ser. No. 155,239, June 21, 1971, abandoned.

[30] Foreign Application Priority Data

June 19, 1970 Spain .................................. 380951
Dec. 30, 1970 United Kingdom ............... 61899/70

[52] U.S. Cl. ................................. 424/331; 424/338

[51] Int. Cl.$^2$ ................ A61K 31/12; A61K 31/075
[58] Field of Search ............................ 424/338, 331

[56] References Cited

OTHER PUBLICATIONS

Schales, Chem. Abst., vol. 46 (1952) p. 11324i.
Zobrist et al., Chem. Abst., vol. 71 (1969) p. 105, 214S.
Weitzel et al., Chem. Abst., vol. 57 (1962) p. 1492b.

*Primary Examiner*—Sam Rosen
*Attorney, Agent, or Firm*—Wenderoth, Lind & Ponack

[57] ABSTRACT

Method for selective cell necrosis in experimental animal tumors by administering a mixture of benzoyl peroxide and 1,2-diphenyl-α,β-diketone into the blood of the animal.

7 Claims, No Drawings

SELECTIVE CELL NECROSIS IN EXPERIMENTAL ANIMAL TUMORS

This application is a division of application Ser. No. 201,331, filed Nov. 23, 1971, now abandoned, which in turn is a continuation-in-part of application Ser. No. 155,239, filed June 21, 1971, now abandoned.

The present invention relates to a process and a preparation for achieving selective cell necrosis in experimental animal tumors, which process and preparation are based on a new principle.

For the present, the inventor has particularly concentrated upon bringing about processes which 1. result in the production of oxidation phenomena or an oxidizing potential in the cells attacked, for instance development of nascent oxygen or hydrogen peroxide, or
2. result in the formation of one or more substances having an antiseptic activity, which are left as a residue in the cells attacked, or which result in both these states.

The substances which the inventor has been interested in are substances which decompose at a pH below 7, since acid conditions prevail in tumor cells in experimental animals.

A number of substances have been investigated and submitted to thorough tests. The inventor has succeeded in proving that the substances mentioned below, administered in the manner described, possess therapeutic activity in experimental animals and have no side effects. All of the substances cause the production of oxidation phenomena as well as the formation of an antiseptic residue.

Substance 1

1,2-Diphenyl-α,β-diketone superoxide, also called benzoyl peroxide. Formula:

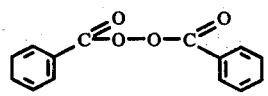

Substance 2

1,2-Diphenyl-α,β-diketone, also called dibenzoyl, diphenyl-glyoxal and 1,2-diphenylethanedione.

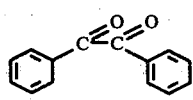

Substance 3

Phenolphthalein, also called 3,3-bis(p-hydroxyphenyl)phthalide and α-(p-hydroxyphenyl)-α-(4-oxo-2,5-cyclohexadien-1-ylidene)-o-toluic acid, or the sodium salt thereof. Formula:

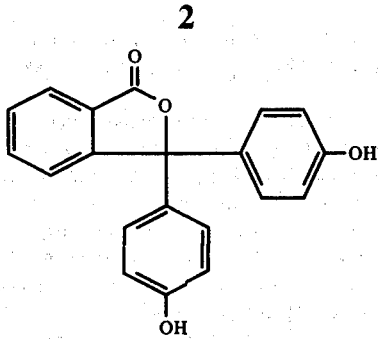

or the sodium salt thereof, i.e.

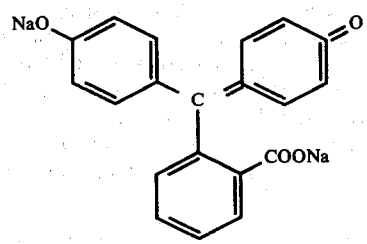

It must be understood that, although only a few specific compounds useful in the method of the present invention have been mentioned, any substance which is capable of performing the same function as those compounds specifically mentioned is acceptable. Thus, those substances which (a) are non-toxic and do not produce harmful side-effects, (b) are oxidants at a pH less than 7 and stable under slightly alkaline conditions and (c) because of the pH and redox-potential conditions in the altered cells, exercise a selective oxidizing effect on the altered cells and deposit an antiseptic substance in the cells, possibly accompanied by the release of nascent oxygen, are acceptable. These substances are all acceptable because, if they do satisfy all these conditions, they ultimately cause the cells to age and thereby advance necrosis.

It has been found that the best way of obtaining contact between the active substances and the sick cells in which processes which are to be controlled are taking place is internal administration, i.e. administration in such a manner that the active substances are brought into the blood. The substances may be directly introduced into the blood or absorbed in the blood through the lymphatic system, whereby all sites within the organism which might be attached are reached.

It has been found to be of importance that the substances are administered in the form of solutions in liposoluble media, such as, for example, oils or fatty acid esters or, in intravenous administration, with, for example polyethylene glycol. These solutions can, of course, contain the usual adjuvants used in pharmacy, such as antiseptics, viscosity-controlling substances, wetting agents, local anesthetics (in preparations for injection), solubilizers, etc.

To summarize, the invention in one aspect resides in a preparation for achieving selective cell necrosis in experimental animal tumors, consisting of a solution, in a liposoluble medium suitable for internal administration, of one or more organic chemical compounds having no or insignificant toxicity, which compounds are capable of, at a pH below 7, undergoing chemical transformation, thereby giving rise to oxidation phenomena.

An especially advantageous preparation consists of a solution as mentioned above containing a substance or substances which by chemical transformation, besides causing oxidation phenomena, form an antiseptic which produces an abiotic selective zone.

Three dispensing forms for the substances 1–3 have been prepared, whereby the substances are caused to circulate in the blood and produce the desired effect: agents for peroral use, agents for injection (intramuscular, hypodermic or intravenous) and suppositories. By these modes of administration the substances are brought into the blood and reach all the tumor cells in experimental animals.

Hereinafter follows a detailed description of the production of preparations containing both the substances 1 and 2 in dissolved form, for oral and parenteral administration, and for administration in the form of suppositories, and of preparations containing the substance 3 in dissolved form, intended for injection. It is to be understood, however, that substances 1 and 2 may be used individually, i.e. without admixture with one another.

Preparations containing the substances Nos. 1 and 2

Use is made of, as solvents, oil or ethyl oleate, both having as little acidity as possible. It must be an oil of good quality or an ethyl oleate having the properties prescribed by the different pharmacopoeiae.

Furthermore, use is made of, as a solvent, polyethylene glycol (M.W. 200), also called plioxyethylene glycol (200), Macrogol 200 and PEG 200 of the formula $CH_2(OH).(CH_2O.CH_2)_m.CH_2OH$, wherein $m$ is 3 or 4. The molecular weight of the substance varies between 185 and 225. Specific gravity is 1.12. It is a clear liquid, colorless, viscous and having a characteristic faint odor. It is soluble in water, alcohol, acetone and in other glycols. It is insoluble in ether and aliphatic hydrocarbons, but soluble in aromatic hydrocarbons.

Use may also be made of other substances possessing properties similar to those of the indicated three solvents.

Preparation for peroral administration

The production method is as follows, with the natural margin and variations allowable for such preparation:

Oil (any which is physiologically acceptable) or ethyl oleate is heated to about 80° C, and under vigorous stirring, from 1 to 4 g % w/v, e.g. 2 g %, of substance No. 2 and afterwards, from 0.5 to 2 g % w/v, e.g. 1 g %, substance No. 1 (dried) are added.

Stirring for about 15 minutes at 80° C is sufficient to dissolve both substances. When the solution is cooled it is ready for use as a peroral drug. If desired, it can be enclosed in capsules.

It should be observed that if the mixture is heated to, e.g. 70° C, instead of 80° C, the dissolution still take place, but in such case stirring for much longer time than 15 minutes is required.

Preparation for intramuscular or hypodermic injection a. A solution as the one described above for oral administration can, in a cooled state, and in a lower dosage, e.g. from 0.5 to 2 g % w/v, e.g. 1 g %, of both substances 1 and 2, with 3% benzyl alcohol being under mechanical stirring, be used a few days, e.g., 4 or 5 days later for intramuscular or hypodermic injection.

b. From 0.5 to 1.5 g % w/w, e.g. 1 g %, of 1,2-diphenyl-$\alpha,\beta$-diketone is dissolved in polyethylene glycol (200), heated to 80° C, under mechanical stirring and immediately afterwards, still at the same temperature, from 0.5 to 1.5 g % w/w, e.g. 1 g %, 1,2-diphenyl-$\alpha,\beta$-diketone superoxide is added and dissolved.

When the substances are dissolved, five minutes being sufficient, the solution is allowed to cool, and when cold, about 3% w/w of benzyl alcohol is added under vigorous stirring.

This solution, filtered and bottled in capped vials or ampoules, can four-five days later be used as an injectable solution for hypodermic or intramuscular injections. This solution should be kept at temperatures between 0° and 5° C until ready for use.

The above-mentioned solution can also be prepared at room temperature under stirring even with a greater concentration of the active substances, the stirring being carried out for a much longer period of time, e.g. 2 hours. The solution is kept in cold storage for subsequent aseptic bottling.

Preparation for intravenous administration

A mixture of polyethylene glycol (200) and half again as much of Tween 80 (polyoxyethylene sorbitol monooleate) is prepared. To this mixture is added 1% w/w of the sodium salt of dioctyl sulfosuccinic acid, and under mechanical stirring there is added to this viscous liquid from 0.2 to 2 g % w/w, e.g. 1 g % of 1,2-diphenyl-$\alpha,\beta$-diketone superoxide and from 0.2 to 2 g % w/w e.g. 1 g %, of 1,2-diphenyl-$\alpha,\beta$-diketone, the order in which the two substances are added making no difference as long as dissolution is effected. 24 hours later (continuous stirring is not necessary, but the mixture should be stirred intermittently), 3 % w/w of benzyl alcohol is added and the liquid is then ready for aseptic bottling in injection ampoules. Both the non-bottled liquid and the injection ampoules are kept in cold storage.

Propylene glycol, vegetable oils and ethyl oleate may also be used in the preparations for intravenous administration.

Preparation for use as suppositories

As a basic mass use can be made of cocoa butter or a synthetic mass such as monolenes, witepsol, etc. In all cases the mass is heated to 80° C, and under mechanical stirring there is added from 1 to 4 g % w/w, e.g. 2 g %, of 1,2-diphenyl-$\alpha,\beta$-diketone and afterwards from 0.5 to 2 g % w/w, e.g. 1 g %, of 1,2-diphenyl-$\alpha,\beta$-diketone superoxide, the temperature being maintained at 80° C. When these substances are dissolved (occurs after stirring for about a quarter hour), the mass is allowed to cool and the suppositories can then be prepared.

Among the above products, cocoa butter is, as known, a natural product prepared on the basis of vegetable fatty acid esters, saturated or unsaturated, with glycerol. Witepsol is a synthetic product, a vegetable fatty acid ester, saturated, with an even number of carbon atoms, with glycerol.

In conformity with that mentioned above, the solution forming the basis of the suppositories may be prepared at a lower temperature, but with a longer stirring period.

The suppositories are to be kept in cold storage until ready for use.

It is also possible to administer the suppositories orally, giving them an appropriate shape.

Preparations containing substance No. 3

Preparation for hypodermic or intramuscular injection

Polyethylene glycol (200) or propylene glycol is heated to 80° C, and under mechanical stirring from 1 to 10% w/w, e.g. 5% of phenolphthalein is dissolved therein. When it is dissolved, the mixture is allowed to cool and, under stirring, 3 % w/w of benzyl alcohol is added, whereafter the liquid is ready for aseptic bottling in capped vials or ampoules and can be used three or four days later.

Preparation for intravenous administration

A mixture of polyethylene glycol (200) and half again as much of Tween 80 (polyoxyethylene sorbitol monooleate) is prepared. 1 % w/w of the sodium salt of dioctyl sulfosuccinic acid is added to the mixture and under continuous stirring there is added to this viscous liquid from 0.4 to 4 % w/w, e.g. 2 %, of phenolphthalein until this is dissolved. After adding to this mixture 3 % w/w of benzyl alcohol, a liquid is obtained which, after filtering and aseptic bottling in ampoules, can be used for intravenous injections.

The recommended dosage is the administration of three fatty cores (via oral means), 4 times a day at meal times: breakfast, lunch, mid-afternoon meal and dinner.

In grave cases, treatment is initiated administering, in addition to the fatty cores, a daily subcutaneous injection in deep fatty areas of 4 c.c., for instance during 1 month.

It is assumed that the mechanism of action of the above mentioned three substances is the following, but the invention is not bound to the correctness of such mechanism;

Substance No. 1.

This substance is, as mentioned, led in to the blood, directly or through the lymphatic system. In the blood at normal pH the substance is stable and circulates dissolved through the organism. When the substance reaches the tumor cells in experimental animals — in the metabolism of which unusually high lactic acid is present — or, in other words, zones of acid pH, the substance liberates nascent oxygen which oxidizes in situ, and simultaneously benzoic acid is produced, which is deposited in the cells.

Substance No. 2.

This substance is also led into the blood, directly or through the lymphatic system. In tumor cells in experimental animals, the substance is by molecular exchange converted into diphenylglycolic acid which then, in these tumor cells, is converted into diphenylacetic acid according to the following:

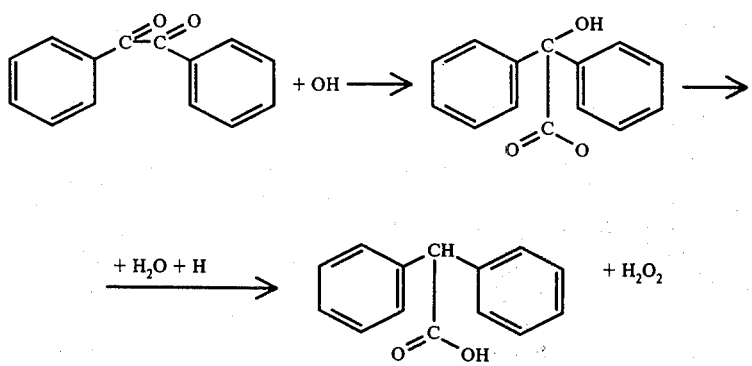

This reaction sequence is supported by the fact that it has been ascertained that an oxidation takes place and that diphenylacetic acid is deposited in the cells.

Substance 3.

This substance circulates in dissolved state in the blood,

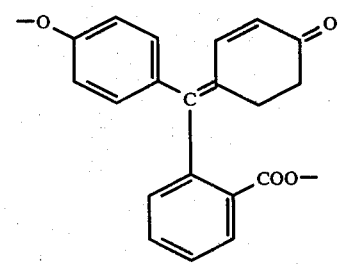

and when it reaches cells having acid zones, liberates

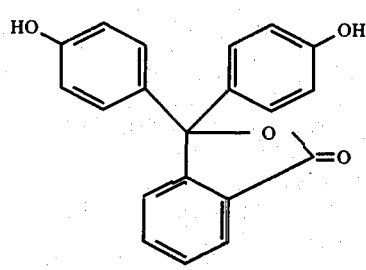

which is more insoluble than the sodium salt. It is strongly antiseptic because of its OH-groups and at the same time possesses oxidizing properties, it being eliminated in the form

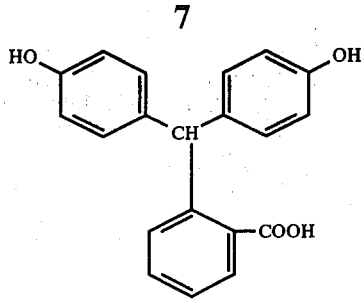

i.e. 4',4''-dihydroxy triphenylmethane-2-carboxylic acid.

It is considered that the substances 1–3 destroy by oxidation, certain components necessary for building up, having a free amino group or free guanidino group, e.g. lysine,

which has a free $\epsilon$-NH$_2$ group, and arginine

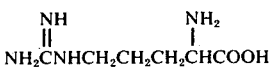

which has a free $\delta$-guanidino group. In support of this, it has been found that histamine in situ at slightly alkaline pH, even at pH 7, is destroyed in a short period of time by oxidation.

It is important to realize that through the use of substances 1–3, or corresponding products, a process of focal necrosis can be produced in test tumors, for example, experimental tumors in animals.

Preparations containing the described substances have been thoroughly tested with regard to their possible toxicity as well as their therapeutic activity.

With toxicity tests, it has been ascertained that the substances are non-toxic. They cause neither tissue alterations nor embryopathic alterations. They do not alter either the circulatory function, nor the electrocardiogram or electroencephalogram. The substances cause no change in the blood picture and they do not change the normal analysis figures. No renal disturbances occur. There are therefore, no contra-indications or side effects which might prevent use of the substances, whether for short- or long-term treatments.

The best results hitherto have been obtained with perparations containing a combination of substances 1 and 2.

The substances 1–3 can be prepared by the usual methods. substance 1 can, for example, be prepared by reaction between benzoyl chloride and a cooled solution of sodium peroxide, cf. A.I. Vogel, *Practical Organic Chemistry*, 3rd ed. (Longmans, London, 1954), p. 807; Gattermann-Wieland, *Praxis de Organischen Chemikers*, 40th ed. (de Gruyter, Berlin, 1961), p. 115.

Substance 2 can be prepared by the oxidation of benzoin with HNO$_3$ or with a copper sulfate-pyridine mixture, cf. e.g. Adams, Marvel, *Org. Syn.* vol. I. p. 25 (1921); Clarke, Dreger, ibid. coll. vol. 1, 80 (87, sec.ed); Hatt, Pilgrim, Hurran, *J. Chem. Soc.* 1936, 93, L. F. Fieser, *Experiments in Organic Chemistry*, 3rd ed. (Boston, 1955), p. 173; *Organic Experiments* (Boston, 1964), p. 214.

Substance 3 can be prepared by condensing phenol with phthalic anhydride in presence of dehydrating agents such as zinc chloride, sulfuric acid, toluenesulfonic acid: Baeyer, Ann. 202, 69 (1880); Herzog, Chem. Ztg. 51, 84 (1927); Hubacher, U.S. Pat. No. 2,192,485; Gamrath, U.S. Pat. No. 2,522,939.

I claim:

1. A method for selective cell necrosis in experimental animal tumors, which comprises administering through the circulatory system to altered cells of an animal having such altered cells a pharmaceutically effective amount of a composition containing benzoyl peroxide and 1,2-diphenyl-$\alpha,\beta$-diketone, and a pharmaceutically suitable carrier therefor, the benzoyl peroxide and 1,2-diphenyl-$\alpha,\beta$-diketone being present in the composition in a pharmaceutically effective ratio.

2. The method according to claim 1, wherein the administration is rectally and the composition is prepared by heating a suitable base mass for suppositories at 80° C, mixing with the base mass, under stirring, from 1 to 4 % w/w of 1,2-diphenyl-$\alpha,\beta$-diketone, and subsequently, under continued stirring, from 0.5 to 2 % w/w of benzoyl peroxide, maintaining the temperature between ambient temperature and 80° C until the mixture is dissolved, cooling the resultant mixture and forming the mixture into suppositories.

3. The method according to claim 1, wherein the administration is perorally and the composition is prepared by heating a suitable base mass at 80° C, mixing with the base mass, under stirring, from 1 to 4 % w/w, of 1,2-diphenyl-$\alpha,\beta$-diketone, and subsequently, under continued stirring, from 0.5 to 2 % w/w of benzoyl peroxide, maintaining the temperature between ambient temperature and 80° C until the mixture is dissolved, cooling the resultant mixture and forming the mixture into a shape suitable for oral administration.

4. The method according to claim 1, wherein the administration is intramuscularly or by hypodermic injection, and the composition is prepared by mixing, under stirring, polyethylene glycol 200 or propylene glycol, heated to a temperature between ambient temperature and 80° C, and from 0.5 to 1.5% w/w of 1,2-diphenyl-$\alpha,\beta$-diketone, immediately thereafter, while maintaining the temperature, adding from 0.5 to 1.5% w/w of benzoyl peroxide, dissolving the compounds, cooling the solution, adding to the cooled solution, under stirring, 3% w/w of benzyl alcohol, filtering the solution and permitting the solution to stand for 4 or 5 days before use.

5. The method according to claim 1, wherein the administration is by intravenous injection, and the composition is prepared by mixing polyethylene glycol 200 and the polyoxyethylene derivative of sorbitan monooleate in a ratio of 1:1.5, adding to the mixture 1% w/w of sodium dioctylsulfosuccinate, adding to the resultant mixture, under stirring, from 0.2 to 2% w/w of benzoyl peroxide and from 0.2 to 2% w/w of 1,2-diphenyl-$\alpha,\beta$-diketone, in optional order, adding, after passage of 24 hours and under occasional stirring, 3% w/w of benzyl alcohol, and filtering the resultant solution.

6. A method for selective cell necrosis in experimental animal tumors, which comprises administering into the blood of an animal having altered cells a pharmaceutically effective amount of a composition containing benzoyl peroxide and 1,2-diphenyl-$\alpha,\beta$-diketone in the form of a solution in a pharmaceutically acceptable liposoluble medium suitable for internal administration, the benzoyl chloride and 1,2-diphenyl-α,β-diketone being present in the composition in a pharmaceutically effective ratio.

7. A composition for achieving selective cell necrosis in experimental animal tumors, comprising benzoyl peroxide, 1,2-diphenyl-α,β-diketone and a pharmaceutically acceptable liposoluble medium, as carrier, suitable for internal administration, the benzoyl peroxide and 1,2-diphenyl-α,β-diketone being present in the composition in a pharmaceutically effective ratio.

* * * * *